(12) United States Patent
Hofland et al.

(10) Patent No.: US 7,906,515 B2
(45) Date of Patent: Mar. 15, 2011

(54) CANCER TREATMENT WITH TOPOISOMERASE-II INHIBITOR, A BIS-DIOXYPIPERAZINE AND RADIATION

(75) Inventors: Kenneth Hofland, Copenhagen (DK); Maxwell Sehested, Copenhagen (DK); Paul Kristjansen, Copenhagen (DK); Annemette Thougaard, Copenhagen (DK); Peter Buhl Jensen, Copenhagen (DK)

(73) Assignee: Topotarget A/S, Copenhagen (DK)

( * ) Notice: Subject to any disclaimer, the term of this patent is extended or adjusted under 35 U.S.C. 154(b) by 0 days.

(21) Appl. No.: 10/591,847

(22) PCT Filed: Mar. 2, 2005

(86) PCT No.: PCT/IB2005/000670
§ 371 (c)(1),
(2), (4) Date: Jan. 9, 2007

(87) PCT Pub. No.: WO2005/084754
PCT Pub. Date: Sep. 15, 2005

(65) Prior Publication Data
US 2007/0185124 A1 Aug. 9, 2007

(30) Foreign Application Priority Data
Mar. 2, 2004 (GB) .................................. 0404675.1

(51) Int. Cl.
*A61K 31/497* (2006.01)
*A61K 31/357* (2006.01)

(52) U.S. Cl. ..................... 514/252.11; 514/252; 514/456

(58) Field of Classification Search .................. 514/34, 514/252, 252.11, 456
See application file for complete search history.

(56) References Cited

U.S. PATENT DOCUMENTS
4,963,551 A * 10/1990 Palepu et al. ............. 514/252.11
6,265,385 B1 * 7/2001 Jensen et al. ..................... 514/34

FOREIGN PATENT DOCUMENTS
WO    WO 97/25044    * 7/1977
WO    97/25044      7/1997

OTHER PUBLICATIONS

International Search Report of PCT/IB2005/000670, mailed Apr. 6, 2006.
Schroeder et al., "Pharmacokinetics of etoposide in cancer patients treated with high-dose etoposide and with dexrazoxane (ICRF-187) as a rescue agent", Cancer Chemotherapy and Pharmacology, vol. 53, No. 1, Jan. 2004, pp. 91-93, XP008061658.
Schroeder et al., "Metabolism of dexrazoxane (ICRF-187) used as a rescue agent in cancer patients treated with high-dose etoposide", Cancer Chemotherapy and Pharmacology, vol. 52, No. 2, Aug. 2003, pp. 167-174, XP008061654.
Holm B et al., "Improved targeting of brain tumors using dexrazoxane rescue of topoisomerase II combined with supralethal doses of etoposide and teniposide", Clinical Cancer Research: An Official Journal of the American Association for Cancer Research, Jun. 1998, vol. 4, No. 6, Jun. 1998, pp. 1367-1373, XP002373086.
Jensen et al., "DNA topoisomerase II rescue by catalytic inhibitors: a new strategy to improve the antitumor selectivity of etoposide", Biochemical Pharamcology, Oct. 1, 1997, vol. 54, No. 7, pp. 755-759, XP008061671.
Holm Bente et al., "ICRF-187 rescue in etoposide treatment in vivo. A model targeting high-dose topoisomerase II poisons to CNS tumors", Cancer Chemoterhapy and Pharmacology, vol. 38, No. 3, 1996, pp. 203-209, XP008061672.
Minehan Kern et al., "The interaction of etoposide with radiation: Variation in cytotoxicity with the sequence of treatment", Life Sciences, vol. 53, No. 15, 1993, pp. 237-242, XP008061879.
Sehested et al, "Antagonistic Effect of the Cardioprotector (+)-1,2-bis(3,5-Dioxopiperazinyl-1-YL)Propane (ICRF-187) on DNA Breaks and Cytotoxicity Induced by the Topoisomerase II Directed Drugs Daunorubicin and Etoposide (VP-16)", Biochemical Pharmacology, vol. 46, No. 3, pp. 389-393, 1993.

* cited by examiner

*Primary Examiner* — Shaojia Anna Jiang
*Assistant Examiner* — Ganapathy Krishnan
(74) *Attorney, Agent, or Firm* — Nixon & Vanderhye P.C.

(57) ABSTRACT

The present invention relates to a method of treatment of a tumour cell which comprises administering to a subject in need of treatment an effective amount of a topoisomerase-II poison, e.g. etoposide, in combination with a bis-dioxypiperazine, e.g. dexrazoxane wherein said subject is further treated with radiation.

3 Claims, 3 Drawing Sheets

Figure 1A:
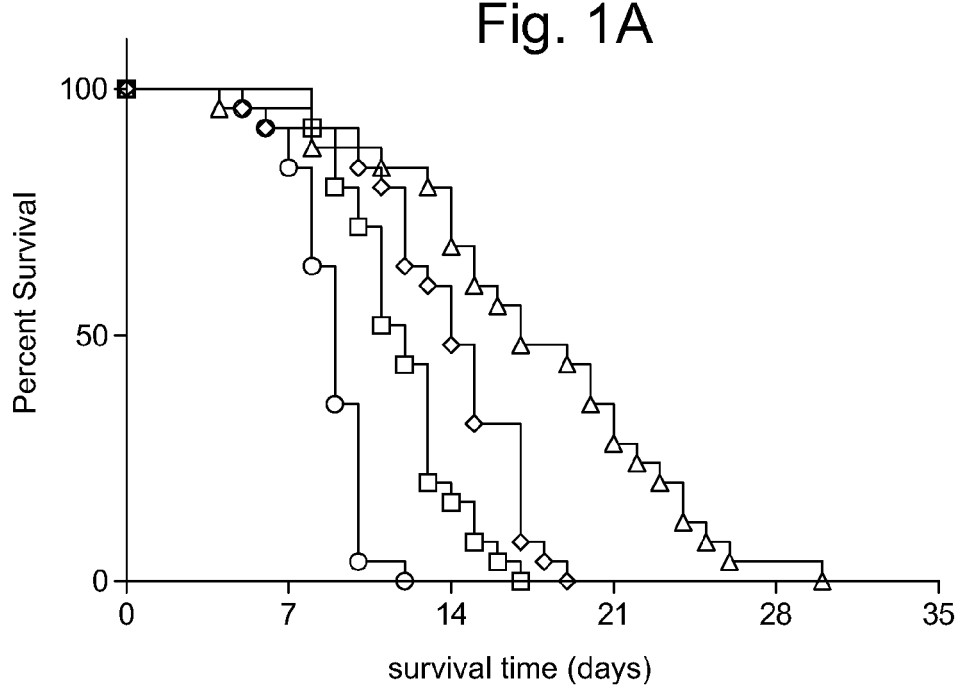

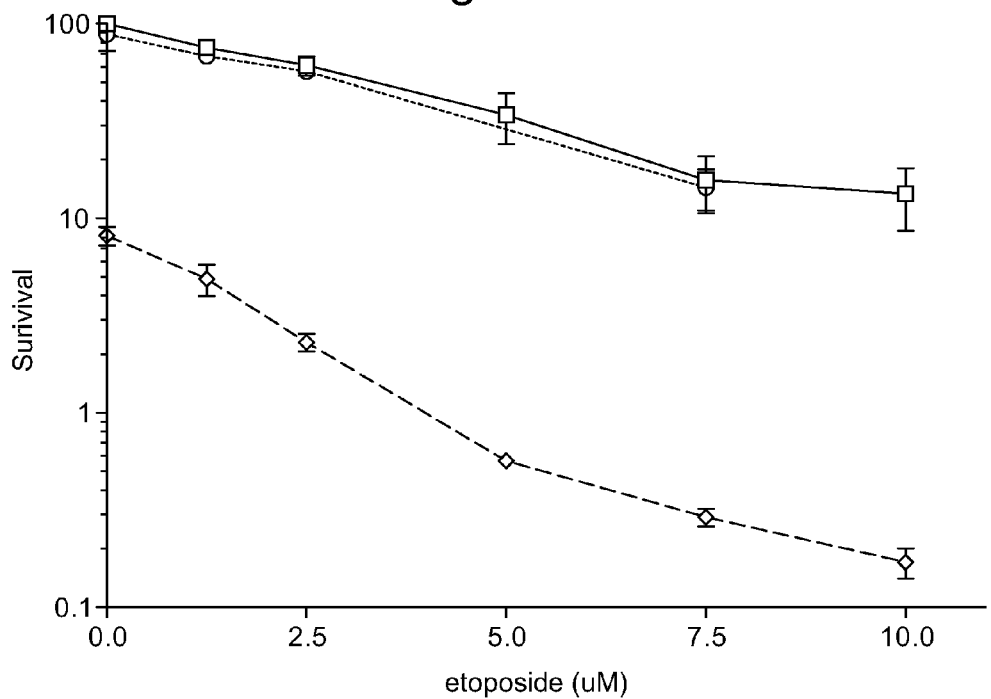
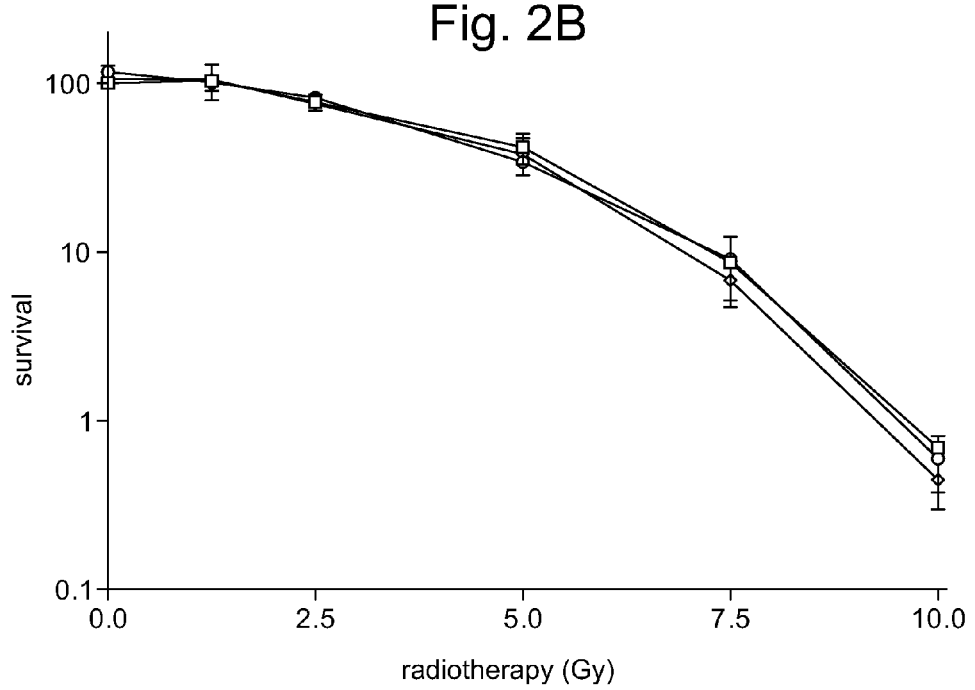

ial application PCT/IB2005/000670, filed 2 Mar. 2005, which designated the U.S. and claims priority of GB 0404675.1, filed 2 Mar. 2004, the entire contents of each of which are hereby incorporated by reference.

CANCER TREATMENT WITH TOPOISOMERASE-II INHIBITOR, A BIS-DIOXYPIPERAZINE AND RADIATION

This application is the US national phase of international application PCT/IB2005/000670, filed 2 Mar. 2005, which designated the U.S. and claims priority of GB 0404675.1, filed 2 Mar. 2004, the entire contents of each of which are hereby incorporated by reference.

FIELD OF THE INVENTION

The present invention relates to the treatment of brain tumours with a triple combination of radiation, a topoisomerase-II inhibitor and a bis-dioxypiperazine, and the to a combination of a topoisomerase-II inhibitor and a bis-dioxypiperazine for use in a method of treatment of a patient with a brain tumour where that patient is undergoing radiation therapy.

BACKGROUND OF THE INVENTION

25% of cancer patients are diagnosed with brain metastases during the course of the disease, with the lung (50%) or breast (20%) as the most frequent site of the primary (1-3). Patients not amenable to local aggressive therapy are offered whole-brain radiotherapy (WBRT), still the mainstay of palliative treatment. Median survival after diagnosis is only 3 to 4 months, and cerebral progression is the course of death in approximately 40% of cases (4-6).

Chemotherapy is often also an option, and among the topoisomerase-II targeted drugs the most widely investigated drugs are e.g. etoposide, teniposide and doxorubicin. These drugs "poison" the nuclear enzyme topoisomerase-II. Topoisomerase-II cleaves and re-ligates double-stranded DNA, allowing the passage of another DNA strand during DNA metabolism (7). Etoposide stabilize the DNA-topoisomerase-II complex in an "open-clamp" conformation and inhibits re-sealing, thus leading to DNA damage, strand breaks and cell death (8).

Besides cytotoxicity via topoisomerase-II, etoposide in combination with radiotherapy also results in synergistic cell-kill in vitro (9-13). Synergy is obtained when drug incubation is simultaneous and post-irradiation, and when critical level of fractional cell-kill is reached, indicating an importance of the doses used. The mechanism behind this interaction is not well known; speculations about interference with DNA damage repair and the fixation of radiation induced damage has not been clarified yet.

The epipodophyllotoxins etoposide and teniposide have been tested in combination with radiotherapy in patients with both primary and metastatic brain tumour, and in SCLC with brain metastases, the response rate was 57% after concurrent WBRT and teniposide compared to 33% after teniposide alone, without increased toxicity though there was no observed increase in survival (14).

Dexrazoxane (ICRF-187) also targets topoisomerase-II, but in contrast to the poisons it catalytically inhibits the enzyme and stabilises a "closed-clamp" conformation of the DNA-topoisomerase-II complex, rendering the enzyme less sensitive to DNA-damage from poisons (15;16).

In vitro, dexrazoxane inhibits the formation of DNA strand breaks induced by topoisomerase-II poisons, and also antagonises toxicity from etoposide in clonogenic assay (17).

WO97/24044 discloses topoisomerase-II poisons in combination with bis-dioxypiperazine derivatives as a combined therapy for the treatment of tumours.

DISCLOSURE OF THE INVENTION

The present inventors have investigated the action of etoposide in combination with dexrazoxane in the treatment of brain tumours in subjects being treated with radiation therapy. It has been found that survival of test animals was surprisingly extended by this triple combination compared to the use of etoposide in conjunction with only one or other of dexrazoxane or radiation therapy alone.

Accordingly, in its first aspect, the present invention provides a method of treatment of a tumour cell which comprises administering to a subject in need of treatment an effective amount of a topoisomerase-II poison in combination with a bis-dioxypiperazine, wherein said subject is further treated with radiation.

In a further aspect, the method provides a topoisomerase-II poison and a bis-dioxypiperazine, as a combined preparation for simultaneous, separate or sequential use in tumour therapy of a patient undergoing radiation treatment.

In another aspect, the invention provides a topoisomerase-II poison, a bis-dioxypiperazine and a source of ionising radiation as a combined preparation for simultaneous, separate or sequential of the topoisomerase-II poison and bis-dioxypiperazine and separate or sequential use of the source of ionising radiation in tumour therapy.

Alternatively, the invention provides a topoisomerase-II poison, a bis-dioxypiperazine and electromagnetic radiation comprising ionising rays as a combined preparation for separate or sequential use in tumour therapy.

The invention also provides the use of a topoisomerase-II poison in combination with a bis-dioxypiperazine for the manufacture of a medicament as a combined preparation for simultaneous, separate or sequential use in the treatment of a patient undergoing radiation therapy for treatment of a tumour.

The invention further provides the use of a topoisomerase-II poison for the manufacture of a medicament in the treatment of a tumour in a subject undergoing radiotherapy, wherein the subject has received treatment with a bis-dioxypiperazine at the time of administration of the topoisomerase-II poison.

The invention further provides the use of a bis-dioxypiperazine for the manufacture of a medicament in the treatment of a tumour in a subject undergoing radiotherapy, wherein the subject has received treatment with a topoisomerase-II poison at the time of administration of the bis-dioxypiperazine.

In another aspect, the invention provides a method of treating a subject with radiotherapy for a tumour, wherein the patient has received a topoisomerase-II poison and a bis-dioxypiperazine within 24 hours prior to treatment.

In another aspect, the invention provides the use of electromagnetic radiation for the manufacture of a medicament for the treatment of a patient who has received a topoisomerase-II poison and a bis-dioxypiperazine within 24 hours prior to treatment.

The subject may be any animal or human subject. Preferably the subject is a human patient. However veterinary applications, such as to large mammals are also contemplated, such as domestic pets such as dogs.

In a particular aspect, the tumour is a tumour of the central nervous system. This includes brain metastases arising out of the spread of a primary tumour such as a small cell lung cancer or a non-small cell lung cancer.

As used herein, reference to treatment includes any treatment for the killing or inhibition of growth of a tumour cell. This includes treatment intended to alleviate the severity of a tumour, such as treatment intended to cure the tumour or to provide relief from the symptoms associated with the tumour. It also includes prophylactic treatment directed at preventing or arresting the development of the tumour in an individual at risk from developing a tumour, particularly in the case of metastases, more particularly in the case of metastases in the CNS. For example, the treatment may be directed to the killing of micro-metastases before they become too large to detect by conventional means.

In another aspect, the invention relates to an in vitro method of treatment of a tumour cell, including metastatic tumour cells such as those of the CNS, wherein the method of treatment comprises the simultaneous, separate or sequential use of a topoisomerase-II poison, a bis-dioxypiperazine and ionising radiation treatment. Such an in vitro method may be conducted on a sample of cells which have been obtained from a patient, so as to determine the response of such cells to the treatment method. The response of the cells may be used to determine whether the patient is likely to respond to therapeutic treatment in accordance with the invention and/or suitable doses of the components of the treatment.

FIGURE LEGENDS

FIGS. 1A, B, C and D show the results of in vivo animal tests:

A: Etoposide 90 mg/kg+dexrazoxane 125 mg/kg (□), 10 Gy (◇), Etoposide 90 mg/kg+dexrazoxane 125 mg/kg and concurrent 10 Gy (Δ) Saline (○). Data are from 3 separate experiments (25 mice in each group).

B: Etoposide 34 mg/kg (□), 10 Gy (◇), Etoposide 34 mg/kg and concurrent 10 Gy (Δ) Saline (○). Data are from 3 separate experiments (26 mice in each group).

C: Etoposide 34 mg/kg+dexrazoxane 125 mg/kg (□), 10 Gy (◇), Etoposide 34 mg/kg+dexrazoxane 125 mg/kg and concurrent 10 Gy (Δ) Saline (○). Data are from 2 separate experiments (18 mice in each group).

D: Dexrazoxane 125 mg/kg (□), 10 Gy (◇), Dexrazoxane 125 mg/kg and concurrent 10 Gy (Δ) Saline (○). Data are from 2 separate experiments (16 mice in each group).

FIGS. 2A and B show semi-logarithmic plots of clonogenic survival after treatment with etoposide or dexrazoxane alone or with concurrent radiotherapy.

Each of the survival curves represent the means of two separate experiments, each plated in triplicates.

Survival was determined as colonies counted after treatment compared to untreated controls. Bars represent the mean value obtained in each of the two experiments.

A: Etoposide alone (□), Etoposide and radiotherapy 1.25 Gy (○), Etoposide and radiotherapy 7.5 Gy (◇) The survival curve after treatment with increasing concentrations of etoposide and fixed dose of 7.5 Gy diverge downwards, indicating supra-additive cell-kill.

B: Radiotherapy alone (□), Radiotherapy and dexrazoxane 25 μM (○), Radiotherapy and dexrazoxane 125 μM (◇). There is no effect at all from combining dexrazoxane and radiotherapy.

DETAILED DESCRIPTION OF THE INVENTION

The present findings indicate that the use of a topoisomerase-II poison and a bis-dioxypiperazine are more effective where these are administered to an environment which is subject to radiation therapy.

By "simultaneous" administration, it is meant that topoisomerase-II poison and a bis-dioxypiperazine are administered to a subject in a single dose by the same route of administration.

By "separate" administration, it is meant that topoisomerase-II poison, a bis-dioxypiperazine and, as the case may be, radiation are administered to a subject by two different routes of administration which occur at the same time. This may occur for example where one component is administered by infusion and the other is given orally during the course of the infusion.

By "sequential" it is meant that the two or three components are administered at different points in time, provided that the activity of the first administered agent is present and ongoing in the subject at the time the second agent is administered. For example, the bis-dioxypiperazine may be administered first, such that its protective effect in non-tumour tissue outside the CNS is established prior to the administration of the topoisomerase-II poison. Both agents may be administered prior to the electromagnetic radiation.

In one embodiment, the three components are administered sequentially, with the bis-dioxypiperazine being administered first, the topoisomerase-II poison second, and the radiation third. Desirably, the topoisomerase-II poison will be administered within 24, preferably within 12, more preferably within 4 and most preferably within 1 hour of administration of the bis-dioxypiperazine.

Alternatively, the topoisomerase-II poison and the bis-dioxypiperazine may be administered simultaneously or separately, followed by administration of the radiation.

In either of the foregoing embodiments, the radiation may be administered sequentially to the administration of whichever of the chemical agents is administered last. Desirably, radiation will be administered within 24, preferably within 12, more preferably within 4 and most preferably within 1 hour of administration of the second chemical agent.

According to the present invention, topoisomerase-II poisons are drugs which include etoposide (VP-16), etoposide-phosphate, teniposide (VM-26) (has a potency which is about 10 fold more potent than VP-16), m-AMSA (m-amsacrine), daunorubicin, and mitoxantrone. Moreover, any topoisomerase II poison which inhibits the relegation step of the nuclear enzyme topoisomerase II at a step where the enzyme has created a cleavable complex in DNA may be used in accordance with the invention.

A preferred topoisomerase-II poison is etoposide 9-[[4,6-O-(1R)-ethylidene-β-D-glucopyranosyl]oxy]-5,8,8a,9-tetrahydro-5-(4-hydroxy-3,5-dimethoxyphenyl)-(5R,5aR,8aR,9S)-furo[3',4':6,7]naphtho[2,3-d]-1,3-dioxol-6(5aH)-one) which may be used in the form of a free compound or salt thereof, particularly a phosphate salt.

The bis-dioxypiperazine compounds, which may be used in the present invention, are bis(3,5-dioxopiperazine-1-yl) alkanes having a structure as shown in the general formula I:

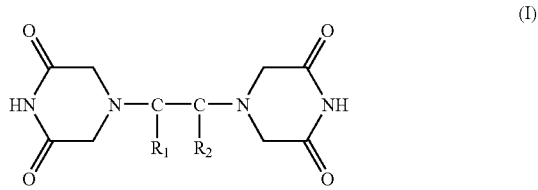

wherein R1 is not the same as R2 and R1 and R2 are hydrogen, or alkyl with 1-4 carbon atoms. The compounds may be in the (−) levo, (+) dextro or (+/−) racemic form. Preferably, R1 is methyl and R2 is hydrogen.

A preferred bis-dioxypiperazine for use in the present invention, is dexrazoxane ((S)-(+)-1,2-Bis(3,5-dioxopiperazin-1-yl)propane), also known as ICRF-187 or Zinecard™.

In the present invention, it is preferred that the combination of the topoisomerase poison and the bis-dioxypiperazine is etoposide and dexrazoxane.

The chemical agents used in the present invention will be formulated appropriately for their desired route of administration. The agent or pharmaceutical composition comprising the agent may be administered to a subject by any convenient route of administration, though usually by injection, particularly intravenous injection.

Doses of the chemical agents and radiation to be administered will ultimately be at the discretion of a physician taking into account the needs of an individual patient.

Generally, topoisomerase II poison will be administered at a dose range of from 1 to 100, for example from 10 to 50, mg/kg body weight of the agent may be administered.

Generally, the bis-dioxypiperazine may be administered at a dose of from about 10 to about 100, for example from 20 to 50 mg/kg body weight.

The amount of radiation to be administered in a dose will be from about 1 to 100 Gy, more preferably from 10 to 50 Gy, which may be given as a series of smaller doses in a dose-fractionated schedule.

The chemical agents for use in the invention may be provided in the form of a pharmaceutical kit, comprising a dosage unit of a bis-dioxypiperazine and a pharmaceutically acceptable carrier and a dosage unit of topoisomerase II poison and a pharmaceutically acceptable carrier. The kit may further comprise the two dosage units in a single infusion system wherein the two dosage units are separated in two individual bags.

The dosage units may comprise the active ingredients as a dry substance, in concentrates suitable for dilution in accordance with the conventional formulation of the drugs, including tablet forms for the topoisomerase II poison.

In one embodiment, the kit comprises the two dosage units in separate containers, e.g. infusion bags which may be administered separately to the patient. In another embodiment, the two containers are connected, e.g. by a Y-shaped tube, to a single infusion tube. Furthermore, additional containers, e.g. comprising neutral fluids, may be connected to the kit whereby the infusion tube may be flushed between the separate infusion of each of the drugs.

Thus in a further aspect, the invention provides a kit as described above for use in a method of treatment of a patient in conjunction with radiation.

The following examples illustrate the invention.

Example

Materials and Methods

Animals:
B6D2F1 female mice from Taconic M&B (Ry, Denmark) were housed in cages of 9 with free access to water and Altromi laboratory diet from Brogaarden (Gentofte, DK). They weighed 19-22 grams at inclusion in protocol. Animals that deteriorated clinically during the experiment were euthanised, and the experiments were approved by the Danish Animal Experimentation Inspectorate.

Tumour Implantation:
A total of $15 \times 10^4$ Ehrlich Ascites tumour cells in 30 uL saline were implanted into the right temporal hemisphere during short CO2 anaesthesia on day 0 and treated on day 3. Treatment was scheduled as follows: dexrazoxane at t=0, etoposide at t=20 minutes and radiation treatment at t=50 minutes. Before the radiotherapy procedure a light anaesthesia was administered, to achieve compliance.

Calculation of Survival Times:
The median survival times obtained after the experimental treatments were expressed as percent of the median survival obtained after radiotherapy, which in all cases was the most effective treatment. This way we obtained a simple and reliable method of comparison.

Efficacy of chemoradiotherapy compared to radiotherapy alone was calculated as:

$$\text{Effect of chemoradiotherapy} = \frac{MS \text{ chemoradiotherapy} - MS \text{ control}}{MS \text{ radiotherapy} - MS \text{ control}} \times 100\% \qquad \text{Eq. 1)}$$

Median survival after chemotherapy compared to radiotherapy alone was calculated as:

$$\text{Effect of chemotherapy} = \frac{MS \text{ chemo} - MS \text{ control}}{MS \text{ radiotherapy} - MS \text{ control}} \times 100\%, \qquad \text{Eq. 2)}$$

The absolute numeric difference in median survival time after chemotherapy alone compared to radiotherapy alone was simply calculated as:

Difference in survival (days)=MS radiotherapy−MS chemotherapy  Eq. 3)

Survival times within the separate experimental treatment groups were compiled, and presented in Kaplan-Meier plots. P-values from Logrank tests comparing survival in experimental groups compared to radiotherapy alone are shown.

In Vitro Experiments:
Following intra-peritoneal treatment with etoposide, approximately 95% of the total etoposide area under the curve is covered within 150 minutes after administration (own experiments, data unpublished). To test if the in vivo effects could be reproduced in vitro, we mimicked the in vivo pharmacokinetics as closely as possible. Ehrlich Ascites tumour cells were incubated in etoposide or dexrazoxane for 30 minutes before irradiation, and then allowed further 120 minutes post-irradiation drug incubation, resulting in a total duration of exposure of 150 minutes. Cells were washed twice in fresh media before plating in soft agar. The number of surviving colonies (>50 cells) were determined after 3 weeks.

Calculation of Interaction:
Survival was normalised to 100%=untreated controls and presented in a semi-logarithmic plot.

The combination index was calculated as proposed by Chou and Talalay (20), using the Calcusyn Software from Biosoft (Cambridge, United Kingdom). It is a prerequisite to calculate the combination index that a dose-effect curve can be obtained for the experimental drugs, and since this was not possible using dexrazoxane, inference of the effect of combination treatment was thus graphical.

Radiotherapy:
X-radiation was generated by a Stabilipan (Siemens, Germany) using 300 kV and 12 mA. The dose-rate was 4.7 Gy/minute.

Drugs and Materials:
Dexrazoxane (Zinecard®) was obtained from Pharmacia (Kalamazoo, Mich.) and further diluted in Ringer-lactate. Etoposide (Vepesid™) was obtained as a ready to administer liquid solution from Pharmacia A/S (Copenhagen, DK) and diluted to final concentration in isotonic saline. 3H-etoposide was obtained from Moravek (Calif., USA) and kept at −20° C. All drugs were administered by the intra-peritoneal (ip.) route.

Histological Evaluation of the Blood Brain Barrier and Blood Tumour Barrier:

Following anaesthesia by hypnorm/dormicum 25 uL of Evans Blue Dye or 80 uL of Lissamine Green was administered by a tail-vein. After allowing the dye to circulate, animals were perfused transcardially with a 4% formalin solution for 5 minutes. The brain was kept in formalin 4%, and 200 uM thick slices were cut on a vibratome and evaluated visually for staining. A check for positive stain of organs was performed before inclusion of the animal in the evaluation of staining of the brain and tumour. Evans Blue Dye and Lissamine Green were obtained from Sigma-Aldrich (Vallensbaek, DK) and prepared fresh as a 2% solution in isotonic saline.

Brain and Tumour Uptake Using Tritiated Etoposide:

Tritium-labelled etoposide was mixed with either "cold" etoposide 9.0 mg/ml, "cold" etoposide 0.9 mg/ml or isotonic saline, all in a final volume of 200 uL. Ten minutes after the administration mice were anaesthetized by $CO_2$, blood was collected and plasma was separated. In addition, one group of mice were pre-treated by dexrazoxane 125 mg/kg similar to the treatment efficacy experiments, and the effect on subsequent etoposide distribution was then assessed as described. Tumour and unaffected contra-lateral brain were removed under a surgical microscope, weighed and sonicated. Activity was measured in a liquid scintillation counter from Packard (US), and counts/gram in brain and tumour was compared to concurrent plasma values.

Results

Dose-Finding and Feasibility Studies:

In initial experiments, mice with brain tumours were treated by radiotherapy alone in doses from 5 Gy to 20 Gy as single shot. The longest median survival time was obtained after 10 Gy. Survival was unaltered after 15 Gy, and 20 Gy added more to toxicity than to tumour control, since we observed that survival time actually decreased compared to that obtained after 10 Gy.

The tolerability of concurrent chemotherapy and radiotherapy was then investigated in healthy mice without tumour. No differences in mortality or morbidity were observed from adding radiotherapy to the various treatment combinations.

Treatment Efficacy Studies:

The survival after radiotherapy alone was superior to chemotherapy alone in all the experiments, and was therefore used as a "standard survival" that other treatment combinations were compared to, as described in methods. Survival after the combination of etoposide 90 mg/kg and dexrazoxane 125 mg/kg with concurrent radiotherapy was significantly increased compared to chemotherapy and radiotherapy alone (Eq. 1) (FIG. 1A). Survival after etoposide 90 mg/kg with dexrazoxane 125 mg/kg was superior to all other chemotherapy treatments tested. The median survival was 60% of that obtained after radiotherapy (table 1), (Eq. 2), and only two days was "lost from ineffective treatment" (Eq. 3).

Though dexrazoxane 125 mg/kg increased survival a little, it still was the worst treatment because 5 days were "lost from ineffective treatment" when compared to radiotherapy (Eq. 3) (table 1).

Figure 1B:
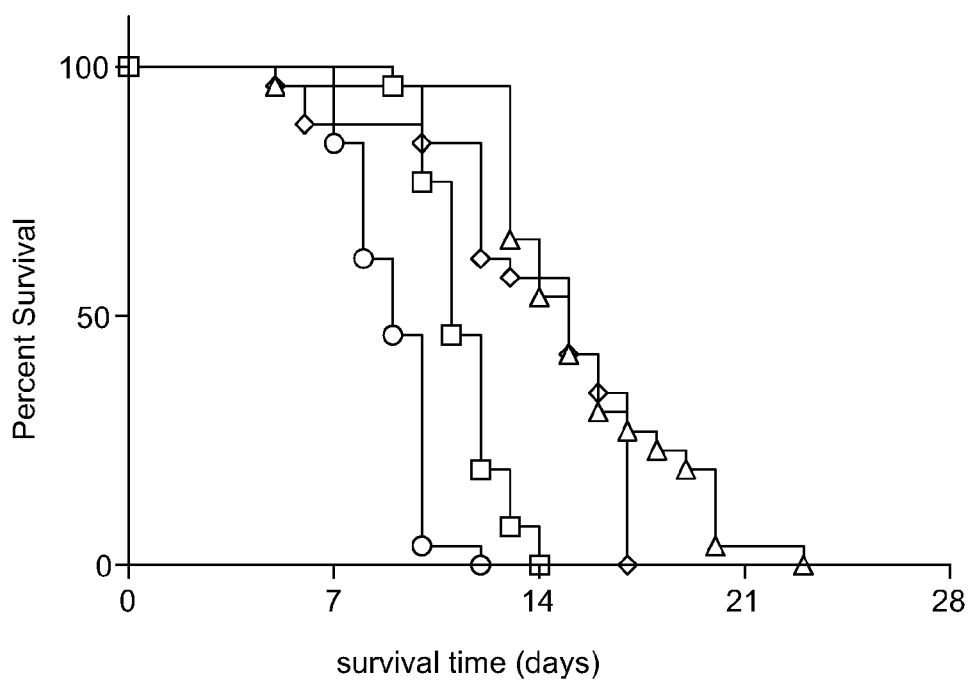
Figure 1C:
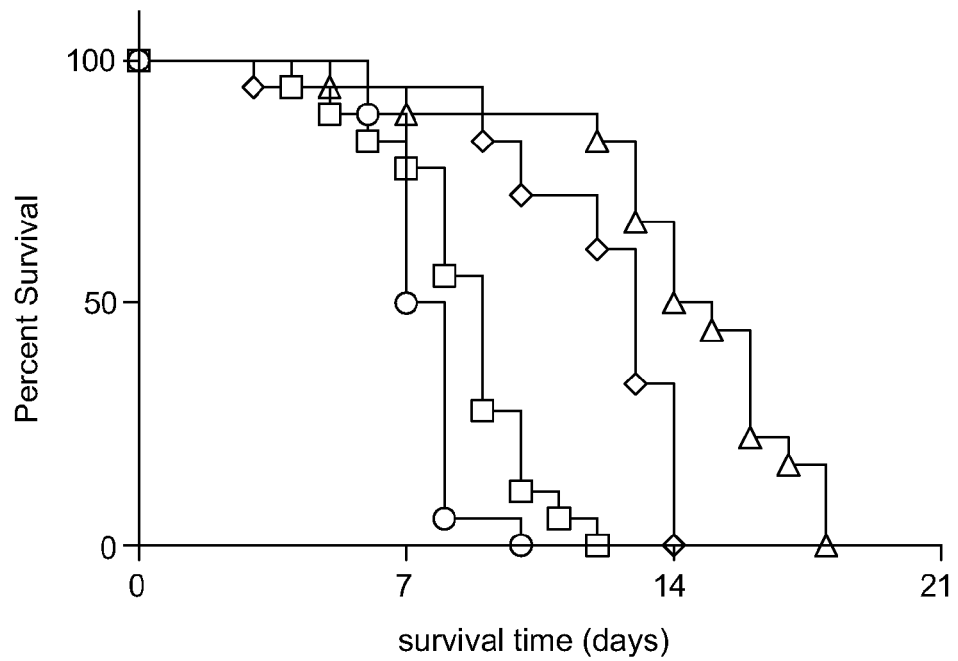

Etoposide 34 mg/kg itself increased survival but did not enhance survival from radiotherapy (FIG. 1B), whereas in the experiments with administration of dexrazoxane 125 mg/kg before etoposide 34 mg/kg there was a small, but significant, effect on the radiotherapy (FIG. 1C).

Figure 1D:
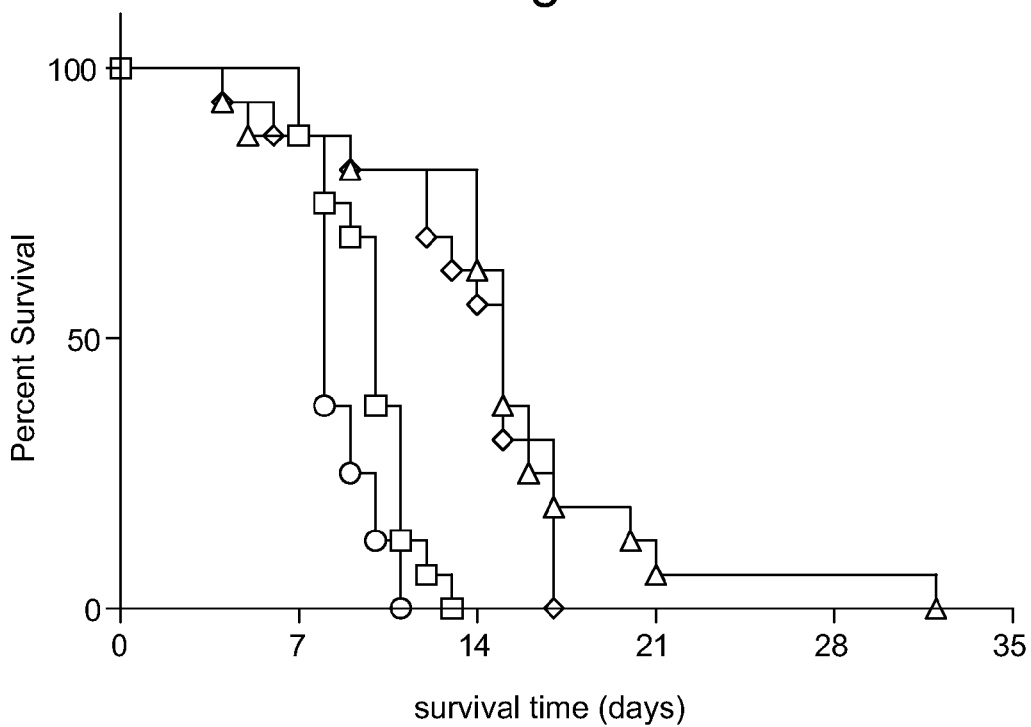

It was also observed that neither dexrazoxane 125 mg/kg (FIG. 1D) nor solvent affected survival in combination with radiotherapy.

Evaluation of the Blood-Brain and Blood-Tumour Barrier by Staining Techniques:

Experiments with Evans blue dye, Lissamine Green and 3H-etoposide were done on day 3, with preparations as described for treatment efficacy experiments.

Mice included in the evaluation were all positively stained outside the brain. Evans blue dye and Lissamine Green were tested separately in 2 groups of 5 mice each. There was no colouration of brain or tumour tissue in either of the groups, suggesting that the integrity of the BBB was intact.

Evaluation of the Brain and Tumour Uptake of 3H-Etoposide:

Neither etoposide dose-escalation nor pre-treatment with dexrazoxane altered the brain/plasma ratio (ANOVA: p=0.37) (table 2).

Tumour drug uptake was higher than in brain, but statistically insignificant, except after treatment with the low dose of etoposide (table 2). As in normal brain, there was no influence on uptake in tumour from the dose of etoposide, vehicle or by pre-pre-treatment with dexrazoxane (ANOVA: p=0.35) (table 2).

In Vitro Combination Treatment:

Increasing concentrations of etoposide were combined with 1.25 Gy or 7.5 Gy, and from the diverging survival curves, synergistic cell-kill was obtained in combination with 7.5 Gy (FIG. 2A).

Calculations of the combination indexes according to the method by Chou and Talalay supported the graphical interpretation: that the degree of synergistic interaction increased with an increase in etoposide dose. It could also be inferred that 1.25 Gy was below a necessary damaging dose, and thus did not result in an increased cell-kill in combination with etoposide (table 3).

Dexrazoxane alone was non-toxic, and the effect of chemoradiotherapy was investigated by combining fixed doses of dexrazoxane with increasing radiotherapy doses. The survival curves from radiation with or without addition of dexrazoxane were almost inseparable, and thus no radio-enhancing effect was obtained (FIG. 2B).

Discussion

The diagnosis of BM is almost invariably fatal, and approximately 40% of patients die as a direct result of progression in the brain. Different doses and schedules of administration of WBRT have been investigated to improve clinical outcome. Survival after 20, 30 and 40 Gy over 2-4 weeks was not better than after 20 Gy in 1 week however (6), and though response duration after single shot 10 Gy and 6 Gy×2 was slightly shorter than after 20 Gy in 1 week, the two treatments were otherwise comparable (21). Attempts at dose-escalating radiotherapy in 153 patients with brain metastases up to 70.4 Gy, with narrowing of the field to the tumour-area from 30 Gy and up, did not affect death from progression in the brain (22).

Efficacy of WBRT in brain metastases has reached a plateau, and the attempts to increase efficacy by adding non-cytotoxics to WBRT has been disappointing with regard to survival (23). A benefit with regard to neurocognitive function was suggested from adding motexafin gadolinium to palliative WBRT in patients with lung cancer (24) and this promising lead is currently investigated in a clinical trial.

Hopefully new targeted drugs can improve treatment efficacy from WBRT (25), but it should be remembered that classic cytotoxics are successful in chemo-radiotherapy protocols (26).

The importance of the blood-brain barrier in clinical oncology is disputed; in SCLC response rates in synchronous brain metastases was ~66% whereas in delayed metastases it was ~36% (27) indicating an intrinsically acquired therapy resistance as a cause of treatment failure, rather than the anatomical localisation.

In breast cancer however, the frequent diagnosis of BM during treatment with HER2 antibody trastuzumab (28) despite similar levels of HER2 expression in tumours inside and outside the brain (29), and is likely caused by poor passage across the blood brain barrier.

Drug uptake, impairment of the blood-brain barrier and the extent of tumour neo-angiogenesis varies locally within experimental tumours (30). Therefore even after obtaining large responses clinically, tumour cells within and immediately outside the area demarked by contrast enhanced imaging still may be insufficiently drug-targeted using standard doses.

In patients with brain metastasis from SCLC, the response rate after WBRT was 50% (31), and after teniposide 150 mg/m$^2$ day 1, 3 and 5 it was 33% (32). In a subsequent comparative phase III trial, teniposide alone resulted in a response rate of 22% compared to 57% after concurrent teniposide and WBRT (14). Likewise, the time to cerebral progression was significantly increased after combination treatment (p=0.005) whereas the median survival was only insignificantly increased from 3.2 to 3.5 months (p=0.087).

This suggests that microscopic tumour cell deposits that reside behind an intact blood brain barrier or in a poorly vascularized part of the tumour was unaffected by the concurrent drug treatment.

Dexrazoxane did not affect the anti-cancer effect from etoposide 34 mg/kg itself (table 1), and in fact the longest survival was obtained after etoposide 90 mg/kg and pretreatment by dexrazoxane 125 mg/kg, and dexrazoxane itself did not affect survival after radiotherapy effect in the in vivo model. Likewise in vitro, dexrazoxane and concurrent radiotherapy did not affect survival compared to radiotherapy alone.

In contrast, etoposide in combination with radiotherapy resulted in synergistic cell-kill in the in vivo model as well in the in vitro experiments.

From the calculations of the combination indexes from the in vitro experiments (table 3) it is seen that at the lowest concentrations of etoposide, the resulting interaction from the combination was in fact antagonistic and that synergism was obtained using increasing concentrations.

The brain/plasma index was unaffected by the etoposide dose, and because the amounts of etoposide and solvent was directly proportional, we were able to conclude that solvent by itself did not affect brain uptake, and further we found that dexrazoxane did not affect the BBB functionality and uptake of etoposide.

We found that the tumour/plasma index was higher than the brain/plasma index but so was also the experimental variability as evidenced by the larger standard deviations, however our data are rather similar to that obtained in patients undergoing surgical resection of brain-tumour after dosing with etoposide (33).

This murine model thus shared important characteristics seen clinically: the more lipophilic drugs crossed the BBB easier than the hydrophilic drugs, the ratio of brain/tumour drug uptake resembled that found in clinical studies, and the increase in survival after WBRT reached a plateau at an optimal radiotherapy dose above which toxicity, but not survival, was increased.

We have shown in vivo that survival is significantly increased after combination treatment with WBRT and etoposide, and that this survival benefit seemed to depend on the tissue drug concentration. Most probable, this observed effect in vivo was a result of a synergistic interaction on the cellular level, since we were able to reproduce it very accurately in the subsequently in vitro experiments.

Our findings leads to two potentially important clinical implications: when combining these two modalities clinically, the importance of achieving relevant tissue concentrations of drug should be kept in mind, and when interpreting outcome from clinical trials using concurrent cerebral radiotherapy and drug treatment, the discrepancies between an increase in overall response and an apparent lack survival benefit could perhaps be explained by differences in concurrent drug concentrations within the radiation field.

All publications and patents mentioned in the above specification are herein incorporated by reference. Various modifications and variations of the described invention will be apparent to those of skill in the art without departing from the scope and spirit of the invention. Although the invention has been described in connection with specific preferred embodiments, it should be understood that the invention as claimed should not be unduly limited to such specific embodiments.

REFERENCES (1) Johnson J D, Young B. Demographics of brain metastasis. Neurosurg Clin N Am 1996; 7(3):337-344.
(2) Patchell R. brain metastasis. In: Vinken P J, Bruyn G W, editors. Handbook of clinical neurology. Elsevier, 1997: pp 135-151.
(3) Takakura K, Sano K, Hojo S, et al. Metastatic tumours of the central nervous system. Tokyo, Igaku-Shoin, 1982: pp 5-35.
(4) Lagerwaard F J, Levendag P C, Nowak P J, Eijkenboom W M, Hanssens P E, Schmitz P I. Identification of prognostic factors in patients with brain metastases: a review of 1292 patients. Int J Radiat Oncol Biol Phys 1999; 43(4):795-803.
(5) Vermeulen S S. Whole brain radiotherapy in the treatment of metastatic brain tumors. Semin Surg Oncol 1998; 14(1): 64-69.
(6) Sheline G E, Brady L W. Radiation therapy for brain metastases. J Neurooncol 1987; 4(3):219-225.
(7) Kellner U, Sehested M, Jensen P B, Gieseler F, Rudolph P. Culprit and victim—DNA topoisomerase II. Lancet Oncol 2002; 3(4):235-243.
(8) Nitiss J L, Beck W T. Antitopoisomerase drug action and resistance. Eur J Cancer 1996; 32A(6):958-966.
(9) Giocanti N, Hennequin C, Balosso J, Mahler M, Favaudon V. DNA repair and cell cycle interactions in radiation sensitization by the topoisomerase II poison etoposide. Cancer Res 1993; 53(9):2105-2111.
(10) Haddock M G, Ames M M, Bonner J A. Assessing the interaction of irradiation with etoposide or idarubicin. Mayo Clin Proc 1995; 70(11):1053-1060.
(11) Iwata T, Kanematsu T. Etoposide enhances the lethal effect of radiation on breast cancer cells with less damage to mammary gland cells. Cancer Chemother Pharmacol 1999; 43(4):284-286.
(12) Minehan K J, Bonner J A. The interaction of etoposide with radiation: variation in cytotoxicity with the sequence of treatment. Life Sci 1993; 53(15):L237-L242.

(13) Ng C E, Bussey A M, Raaphorst G P. Inhibition of potentially lethal and sublethal damage repair by camptothecin and etoposide in human melanoma cell lines. Int J Radiat Biol 1994; 66(1):49-57.

(14) Postmus P E, Haaxma-Reiche H, Smit E F, Groen H J, Karnicka H, Lewinski T et al. Treatment of brain metastases of small-cell lung cancer: comparing teniposide and teniposide with whole-brain radiotherapy—a phase III study of the European Organization for the Research and Treatment of Cancer Lung Cancer Cooperative Group. J Clin Oncol 2000; 18(19):3400-3408.

(15) Roca J, Ishida R, Berger J M, Andoh T, Wang J C. Antitumor bisdioxopiperazines inhibit yeast DNA topoisomerase II by trapping the enzyme in the form of a closed protein clamp. Proc Natl Acad Sci U S A 1994; 91(5):1781-1785.

(16) Sehested M, Jensen P B. Mapping of DNA topoisomerase II poisons (etoposide, clerocidin) and catalytic inhibitors (aclarubicin, ICRF-187) to four distinct steps in the topoisomerase II catalytic cycle. Biochem Pharmacol 1996; 51(7):879-886.

(17) Sehested M, Jensen P B, Sorensen B S, Holm B, Friche E, Demant E J. Antagonistic effect of the cardioprotector (+)-1,2-bis(3,5-dioxopiperazinyl-1-yl)propane (ICRF-187) on DNA breaks and cytotoxicity induced by the topoisomerase II directed drugs daunorubicin and etoposide (VP-16). Biochem Pharmacol 1993; 46(3):389-393.

(18) Holm B, Jensen P B, Sehested M. ICRF-187 rescue in etoposide treatment in vivo. A model targeting high-dose topoisomerase II poisons to CNS tumors. Cancer Chemother Pharmacol 1996; 38(3):203-209.

(19) Holm B, Sehested M, Jensen P B. Improved targeting of brain tumors using dexrazoxane rescue of topoisomerase II combined with supralethal doses of etoposide and teniposide. Clin Cancer Res 1998; 4(6):1367-1373.

(20) Chou T-C, Talalay P. Analysis of combined drug effects: a new look at a very old problem. Trends in Pharmacological Science 1983; November, pp. 450-454.

(21) Borgelt B, Gelber R, Larson M, Hendrickson F, Griffin T, Roth R. Ultra-rapid high dose irradiation schedules for the palliation of brain metastases: final results of the first two studies by the Radiation Therapy Oncology Group. Int J Radiat Oncol Biol Phys 1981; 7(12):1633-1638.

(22) Epstein B E, Scott C B, Sause W T, Rotman M, Sneed P K, Janjan N A et al. Improved survival duration in patients with unresected solitary brain metastasis using accelerated hyperfractionated radiation therapy at total doses of 54.4 gray and greater. Results of Radiation Therapy Oncology Group 85-28. Cancer 1993; 71(4):1362-1367.

(23) Komarnicky L T, Phillips T L, Martz K, Asbell S, Isaacson S, Urtasun R. A randomized phase III protocol for the evaluation of misonidazole combined with radiation in the treatment of patients with brain metastases (RTOG-7916). Int J Radiat Oncol Biol Phys 1991; 20(1):53-58.

(24) Meyers C A, Smith J A, Bezjak A, Mehta M P, Liebmann J, Illidge T et al. Neurocognitive function and progression in patients with brain metastases treated with whole-brain radiation and motexafin gadolinium: results of a randomized phase III trial. J Clin Oncol 2004; 22(1):157-165.

(25) Ma B B, Bristow R G, Kim J, Siu L L. Combined-modality treatment of solid tumors using radiotherapy and molecular targeted agents. J Clin Oncol 2003; 21(14):2760-2776.

(26) Curran W J. New chemotherapeutic agents: update of major chemoradiation trials in solid tumors. Oncology 2002; 63 Suppl 2:29-38.

(27) Grossi F, Scolaro T, Tixi L, Loprevite M, Ardizzoni A. The role of systemic chemotherapy in the treatment of brain metastases from small-cell lung cancer. Crit Rev Oncol Hematol 2001; 37(1):61-67.

(28) Bendell J C, Domchek S M, Burstein H J, Harris L, Younger J, Kuter I et al. Central nervous system metastases in women who receive trastuzumab-based therapy for metastatic breast carcinoma. Cancer 2003; 97(12):2972-2977.

(29) Fuchs I B, Loebbecke M, Buhler H, Stoltenburg-Didinger G, Heine B, Lichtenegger W et al. HER2 in brain metastases: issues of concordance, survival, and treatment. J Clin Oncol 2002; 20(19):4130-4133.

(30) Simpson-Herren L, Noker P E, Wagoner S D. Variability of tumor response to chemotherapy. II. Contribution of tumor heterogeneity. Cancer Chemother Pharmacol 1988; 22(2):131-136.

(31) Postmus P E, Haaxma-Reiche H, Gregor A, Groen H J, Lewinski T, Scolard T et al. Brain-only metastases of small cell lung cancer; efficacy of whole brain radiotherapy. An EORTC phase II study. Radiother Oncol 1998; 46(1):29-32.

(32) Postmus P E, Smit E F, Haaxma-Reiche H, van Zandwijk N, Ardizzoni A, Quoix E et al. Teniposide for brain metastases of small-cell lung cancer: a phase II study. European Organization for Research and Treatment of Cancer Lung Cancer Cooperative Group. J Clin Oncol 1995; 13(3):660-665.

(33) Zucchetti M, Rossi C, Knerich R, Donelli M G, Butti G, Silvani V et al. Concentrations of VP16 and VM26 in human brain tumors. Ann Oncol 1991; 2(1):63-66.

The invention claimed is:

1. A method of treatment of a tumour cell in the brain which comprises administering to a subject in need of treatment an effective amount of a topoisomerase-II poison in combination with a bis-dioxypiperazine, wherein said subject is further treated with brain radiation therapy:

wherein the bis-dioxypiperazine is dexrazoxane;

wherein the topoisomerase-II poison is selected from the group consisting of etoposide, etoposide phosphate, teniposide, m-amsacrine, daunorubicin and mitoxantrone;

wherein the topoisomerase-II poison is administered at a dose range of from 1 to 100 mg/kg body weight and the bis-dioxypiperazine is administered at a dose range of from about 10 to about 100 mg/kg body weight; and wherein the radiation is administered at a dose of from about 1 to 100 Gy.

2. A method according to claim 1 wherein the topoisomerase-II poison is etoposide.

3. A method according to claim 1, wherein the tumour is a CNS tumour.

* * * * *